United States Patent [19]

Baldwin et al.

[11] Patent Number: 4,574,127

[45] Date of Patent: Mar. 4, 1986

[54] OXAZOLES AND THIAZOLES CONTAINING AN AMINOHYDROXYPROPOXYPHENYL MOIETY

[75] Inventors: John J. Baldwin, Gwynedd Valley; Gerald S. Ponticello, Lansdale, both of Pa.

[73] Assignee: Merck & Co., Inc., Rahway, N.J.

[21] Appl. No.: 607,906

[22] Filed: May 7, 1984

[51] Int. Cl.$^4$ .................. C07D 277/28; C07D 263/32; A61K 31/42; A61K 31/425
[52] U.S. Cl. .................................. 514/365; 514/374; 548/205; 548/235
[58] Field of Search ................ 548/205, 235; 514/365, 514/374

[56] References Cited

U.S. PATENT DOCUMENTS 4,134,983  1/1979  Baldwin .............................. 424/267

FOREIGN PATENT DOCUMENTS 39892    11/1981  European Pat. Off. ............ 424/270
3006351   9/1981  Fed. Rep. of Germany ...... 424/270
WO84/1945 5/1984  PCT Int'l. Appl. ................. 424/270

OTHER PUBLICATIONS

Crowther et al., J. Med. Chem. 15 260 (1972).

*Primary Examiner*—Robert Gerstl
*Attorney, Agent, or Firm*—Alice O. Robertson; Salvatore C. Mitri

[57] ABSTRACT

Novel substituted aminohydroxypropoxyphenyl oxazole and thiazole compounds and methods for their preparation are disclosed. These compounds, and their salts exhibit cardioselective β-adrenergic blocking activity, and are useful as antihypertensive, cardioprotective, antiarrhythmic and antianginal agents.

3 Claims, No Drawings

OXAZOLES AND THIAZOLES CONTAINING AN AMINOHYDROXYPROPOXYPHENYL MOIETY

BACKGROUND OF THE INVENTION

The present invention is directed to novel aminohydroxypropoxyphenyl oxazole and thiazole compounds which have cardioselective β-adrenergic blocking activity and which are useful as antihypertensive agents, cardioprotective agents, antiarrythmic agents, and antianginal agents.

A class of pharmaceutical agents, known as β-adrenergic blocking agents, are available and are known to affect cardiac, vascular and pulmonary functions and are mild antihypertensives. Specifically, these known β-adrenergic blocking agents have the capability of reducing heart rate, without counteracting vasodepression or suppressing bronchodilation. β-adrenergic blocking agents, their chemical structure and activity, are generally disclosed in "Clinical Pharmacology and Therapeutics" 10, 292-306 (1969). Various β-adrenergic blocking agents are also described in such patents as, for example, U.S. Pat. No. 3,048,387; U.S. Pat. No. 3,337,628; U.S. Pat. No. 3,655,663; U.S. Pat. No. 3,794,650; U.S. Pat. No. 3,832,470; U.S. Pat. No. 3,836,666; U.S. Pat. No. 3,850,945; U.S. Pat. No. 3,850,946; U.S. Pat. No. 3,850,947; U.S. Pat. No. 3,852,291 and British Pat. No. 1,194,548.

U.S. Pat. Nos. 4,134,983 and 4,199,580 also disclose a class of substituted imidazoles which have β-adrenergic blocking activity.

SUMMARY OF THE INVENTION

A novel class of substituted aminohydroxypropoxyphenyl oxazole and thiazole compounds has been discovered which exhibit cardioselective β-adrenergic blocking activity and, by virtue of their β-blocking activity, also exhibit antihypertensive, cardioprotective, antiarrhythmic and antianginal activity and are also useful as ophthalmic agents in the treatment of glaucoma.

DESCRIPTION OF PREFERRED EMBODIMENTS

The compounds of the present invention are represented by the general formula:

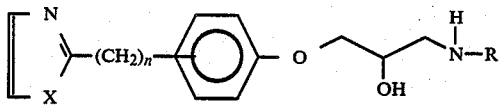

wherein:
X is oxygen or sulfur;
R is $C_1$–$C_8$ linear or branched alkyl; $C_3$–$C_6$cycloalkyl; unsubstituted or substituted aralkyl wherein the alkyl group is linear or branched $C_1$–$C_8$ and the aryl is $C_6$ having 1-2 substituents selected from $C_1$–$C_8$alkoxy, hydroxy, halo (F, Br, Cl), $C_1$–$C_8$alkyl; heteroaralkyl having 6 ring atoms containing 1-2N heteroatoms and the alkyl is $C_1$–$C_8$; substituted $C_1$–$C_8$alkyl having 1-2 substituents selected from $C_1$–$C_8$alkoxy, thioalkyl of $C_1$–$C_8$, ureido, substituted ureido having the formula:

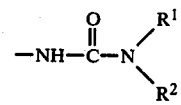

wherein $R^1$ and $R^2$ can independently be hydrogen, $C_1$–$C_8$ alkyl optionally substituted with hydroxy, $C_1$–$C_8$ alkoxy, unsubstituted or substituted aryl of $C_6$ or $C_{10}$ wherein the substituent is $C_1$–$C_4$ alkyl, or $R^1$ and $R^2$ together with the N atom can be joined to form a 6-membered heteroaryl group which may optionally contain an additional O, S or N-lower $C_1$–$C_6$ alkyl heteroatom;
n is 0, 1, 2 or 3;
and, the pharmacologically acceptable acid addition salts thereof.

Exemplary 6-membered heteroaryl groups attached to the alkyl group of R include 2-pyridyl, 3-pyridyl, 4-pyridyl, 2-pyrazinyl, 2-pyrimidinyl, 4-pyrimidinyl, 5-pyrimidinyl, 3-pyridazinyl, 4-pyridazinyl, and the like.

Illustrative aryl groups in the R aralkyl moiety include 3,4-dimethoxyphenyl, 3,4-di-n-butoxyphenyl, 3,4-methylenedioxyphenyl, 3-hydroxy-4-methoxyphenyl, 3-methoxy-4-hydroxyphenyl, 3,4-dihydroxyphenyl, 3-hydroxyphenyl, 3-methoxyphenyl, 4-hydroxyphenyl, 4-methoxyphenyl, 2-ethoxyphenyl, 2-hydroxyphenyl, 3,4-dichlorophenyl, 3,5-dibromophenyl, 3-hydroxy-4-chlorophenyl, 4-chloro-3-hydroxyphenyl, 4-fluorophenyl, 4-hexyloxyphenyl, 3-methylphenyl, 3,4-dimethylphenyl, and the like.

Illustrative $R^1$ and $R^2$ groups include methyl, ethyl, n-butyl, hydroxyethyl, methoxybutyl, phenyl, benzyl, and the like, and when $R^1$ and $R^2$ are joined together with the N-atom, they form such hetero rings as

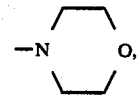

and the like.

Preferred are those compounds of Formula I wherein:
X is oxygen or sulfur;
R is $C_3$–$C_5$ cycloalkyl; $C_1$–$C_8$ linear or branched alkyl; unsubstituted or substituted aralkyl wherein the alkyl is linear or branched $C_1$–$C_8$ and the aryl is $C_6$ or $C_{10}$ having 1-2 substituents selected from $C_1$–$C_8$ alkoxy, hydroxy, halo, $C_1$–$C_8$ alkyl; heteroaralkyl having 6-ring atoms containing 1-2N heteroatoms and wherein the alkyl group is $C_1$–$C_4$; and,
n is 0-2.

More preferred are those compounds of Formula I wherein:
X is oxygen or sulfur;
R is $C_3$–$C_5$ cycloalkyl; unsubstituted or substituted aralkyl wherein the alkyl is linear or branched $C_1$–$C_8$ and the aryl is $C_6$ or $C_{10}$ having 1-2 substituents selected from $C_1$–$C_8$ alkoxy, hydroxy, halo, $C_1$–$C_8$ alkyl;
n is 0; and,
the phenylene is bonded at its 1 and 4 positions.

The compounds of the present invention include the N-oxides and the non-toxic pharmacologically acceptable acid addition salts thereof. The acid addition salts are prepared by treating the compounds of the invention with an appropriate amount of a suitable organic or inorganic acid. Examples of useful organic acids are carboxylic acids such as maleic acid, tartaric acid, acetic acid, pamoic acid, oxalic acid, propionic acid, salicylic acid, succinic acid, citric acid, malic acid, isethionic acid, and the like; useful inorganic acids are hydrohalo acids such as HCl, HBr and HI, sulfuric acid, $H_3PO_4$, and the like.

The compounds of the present invention include all the optical isomer forms. In other words, the compounds include mixtures containing the optical isomers such as racemic mixtures, as well as the individual optical isomers.

Compounds of the present invention can be prepared by the methods shown in the following Reaction Scheme wherein X, R and n are as defined above unless otherwise indicated.

REACTION SCHEME

METHOD A

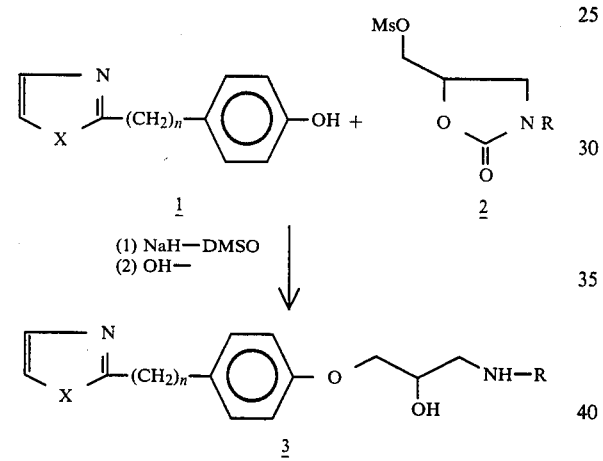

As shown in Method A above, phenol 1 is first reacted with a base and the oxazolidone mesylate 2 [prepared according to the methods disclosed in Canadian Patent No. 965,787] or any other suitable leaving group such as a tosylate, triflate, or iodide, in the presence of sodium hydride, sodium methoxide, sodium hydroxide, potassium t-butoxide, and the like, in a suitable solvent such as dimethylsulfoxide (DMSO), dimethylformamide (DMF), toluene, methanol, water, and the like, at a temperature of about 0° C. to the reflux temperature of the solvent for a period of about 1-48 hours, preferably using sodium hydride in DMSO at about 60° C. for about 2 hours. The hydrolysis of the oxazolidone intermediate proceeds with an aqueous base such as sodium hydroxide, potassium hydroxide, and the like, at a concentration of about 1-40% in an appropriate co-solvent such as methanol ($CH_3OH$), ethanol (EtOH; $CH_3CH_2OH$), acetone, tetrahydrofuran (THF), and the like, preferably 10% NaOH-EtOH at 1:1, at the reflux temperature of the solvent over a period of about 15 minutes-2 hours, preferably for about 2 hours at reflux, to afford a compound 3 of the invention.

METHOD B

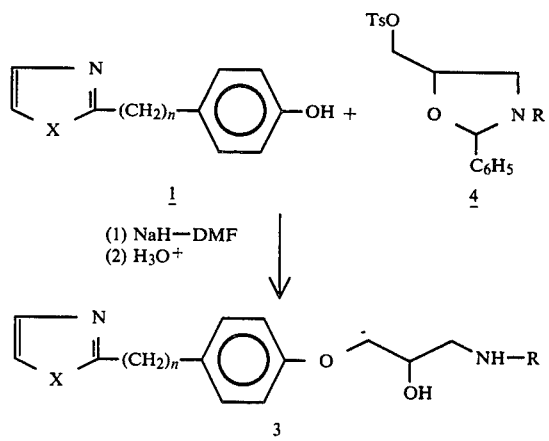

In Method B, phenol 1 is reacted with the oxazolidine tosylate 4 or any other suitable leaving group such as a mesylate, triflate, or iodide, and a base such as sodium hydride, sodium methoxide, sodium hydroxide, potassium t-butoxide, and the like, preferably sodium hydride, in a suitable solvent such as DMSO, DMF, toluene, $CH_3OH$, $H_2O$, and the like, preferably in DMF, at about 0° C. to the reflux temperature of the solvent for about 1-48 hours, preferably at 100° C. for 18 hours, to obtain an oxazolidine intermediate. The oxazolidine intermediate is then subjected to acid hydrolysis using such acid as aqueous HCl, aqueous $H_2SO_4$, acetic acid, and the like, at about 0° C. to the reflux temperature of the solvent for about 15 minutes-15 hours, preferably in 1N HCl at 100° C. for 30 minutes, to afford a compound 3 of the invention.

METHOD C

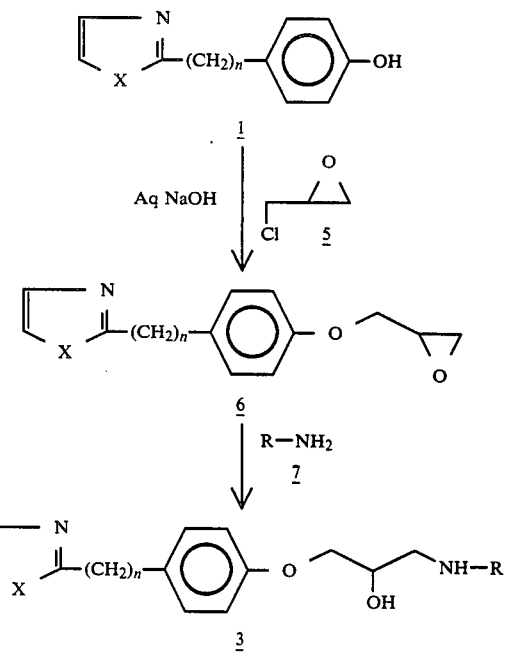

In Method C, phenol 1 is treated with epichlorohydrin 5 in a suitable solvent such as $H_2O$, $CH_3OH$, EtOH, and the like, in the presence of a base such as sodium hydroxide, potassium hydroxide, piperidine, potassium t-butoxide, and the like, at a temperature of about 0° C. to the reflux temperature of the solvent, preferably using aqueous 2.5N sodium hydroxide at 50° C. for 15 hours, to yield epoxide 6. Treatment of 6 with an amine 7 in an appropriate solvent such as THF, methylene chloride ($CH_2Cl_2$), isopropanol (iso-Pro), and the like, at about 0° C. to the reflux temperature of the solvent for about 1–48 hours, preferably in iso-Pro at 70° C. for 15 hours, affords a compound 3 of the invention.

The compounds of the present invention are active as cardioselective β-adrenergic blocking agents and are useful as antihypertensive, cardioprotective, antiarrhythmic, and antianginal agents.

The β-adrenergic blocking effectiveness of the compounds of the present invention indicates that they are also useful to treat humans suffering from undesirable conditions such as hypertension, angina pectoris or certain arrhythmias which are known to be amenable to treatment with β-adrenergic blocking agents. Thus, the compounds of the invention are useful as antihypertensive, cardioprotective, antiarrhythmic, and antianginal agents. Furthermore, the cardioselective nature of the compounds of the present invention offers the advantage of limiting blockade to only the $\beta_1$ receptors; i.e., those which control heart rate. Thus, these β-blocking agents are also useful to control tachycardia which may be drug induced (as by isoproterenol) or brought about by physiological conditions, reduce intraocular pressure in the treatment of glaucoma, and inhibit renal renin secretion.

For use as antihypertensives and/or β-adrenergic blocking agents, the present compounds can be administered orally, transdermally or parenterally; i.e., intravenously, interperitoneally, etc. and in any suitable dosage form. The compounds may be offered in a form (a) for oral administration; e.g., as tablets, in combination with other compounding ingredients customarily used such as talc, vegetable oils, polyols, benzyl alcohols, gums, gelatin, starches and other carriers; dissolved or dispersed or emulsified in a suitable liquid carrier; in capsules or encapsulated in a suitable encapsulating material; or (b) for parenteral administration; e.g., dissolved or dispersed in a suitable liquid carrier or emulsified; or (c) for transdermal application. The ratio of active compound to compounding ingredients; i.e., carrier, diluent, etc., will vary as the dosage form requires. Whatever dosage form is used, the amount of compound of the present invention administered should be sufficient to effect (a) a reduction in blood pressure of the patient suffering from hypertension and/or (b) desirable level of β-blockade in the patient. Generally, doses of the present compounds can be administered in amounts of from about 1 mg to about 1 g and preferably from about 5 to about 500 mg per day. Dosage may be single or multiple depending on the daily total required and the unit dosage.

Following are examples illustrating representative pharmaceutical formulations containing compounds of the present invention. Conventional techniques are used to prepare these formulations.

| INGREDIENT | AMOUNT (Mg.) |
| --- | --- |
| TABLET FORMULATION | |
| 2-{p-[3-(3,4-dimethoxyphenethylamino)-2-hydroxypropoxy]phenyl}oxazole | 40.0 |
| calcium phosphate | 120.0 |
| lactose | 50.0 |
| starch | 23.5 |
| magnesium stearate | 1.5 |
| CAPSULE FORMULATION | |
| (S) 2-{p-[3-(3,4-dimethoxyphenyl-ethyl)amino)-2-hydroxypropoxy]-phenyl}thiazole | 250 |
| lactose, U.S.P. | 93 |
| talc | 7 |
| LIQUID SUSPENSION | |
| 2-[p-(3-cvclopropoxyamino-2-hydroxypropoxy)phenyl]thiazole | 5.0 |
| Veegum H.V. | 3.0 |
| methyl paraben | 1.0 |
| kaolin | 10.0 |
| glycerin | 250.0 |
| water, q.s. | 1 liter |
| OCULAR FORMULATION | |
| (S) 2-{p-[3-(3,4-dimethoxyphenyl-ethyl)amino-2-hydroxypropoxy]phenyl}thiazole | 15.0 |
| sodium phosphate monobasic .2 $H_2O$ | 6.10 |
| dibasic sodium phosphate .12 $H_2O$ | 16.80 |
| benzalkonium chloride | 0.10 |
| sodium hydroxide q.s. | ph 6.8 |
| water for injection q.s. ad. | 1.0 ml |

The following examples illustrate preparation of representative compounds of the present invention. Unless otherwise indicated, all parts and percentages are by weight, all temperatures are in degrees Celsius, and all analyses were computed to within 0.4%.

EXAMPLE 1

2-{p-[3-(3,4-Dimethoxyphenethylamino)-2-hydroxypropoxy]phenyl}oxazole (4)

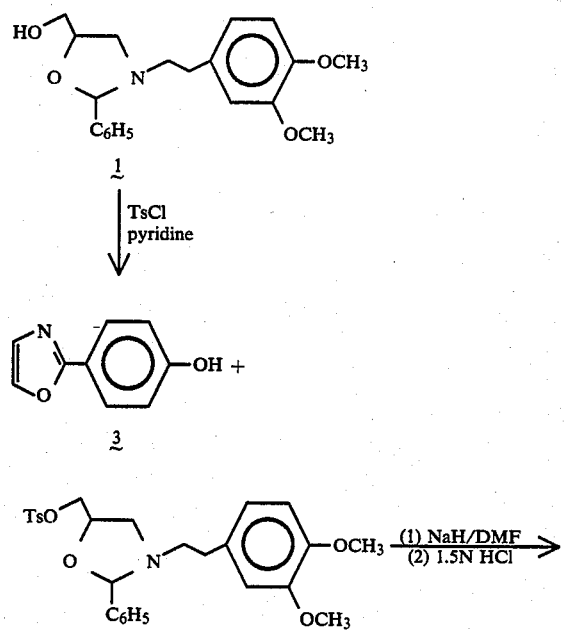

7

-continued

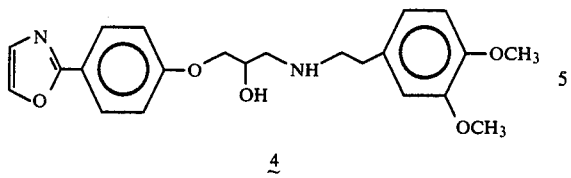

A solution of 2-phenyl-3-(3,4-dimethoxyphenyle-thyl)-5-(hydroxymethyl)oxazolidine 1 (25.76 g, 0.075 m) in pyridine (30 ml) was cooled to 10° C. and p-toluenesulfonyl chloride (14.30 g, 0.075 m) was added over 30 minutes, keeping the temperature below 25° C. After stirring at 25° C. for 3 hours, a cold solution of $K_2CO_3$ (10.37 g, 0.075 m) in $H_2O$ (70 mL) was added and the mixture was extracted with $CHCl_3$ (3×125 mL). The extracts were washed with $H_2O$, dried and concentrated under reduced pressure below 50° C., initially using water aspiration and finally high vacuum to yield the tosylate 2 (35.83 g, 96%). Sodium hydride (3.36 g, 0.070 m, 50% dispersion in mineral oil) was added to a solution of p-(2-oxazolyl)phenol 3 (11.29 g, 0.070 m) prepared according to the procedure of H. Jones, et al. [J. Med. Chem., 21, 1100 (1978)] in dimethylformamide (125 mL) under nitrogen and the mixture was heated at 60° C. for 30 min. A solution of the tosylate 2 (35.83 g., 0.072 m) in dimethylformamide (110 mL) was added and the mixture was refluxed for 16 hours. The solvent was removed under reduced pressure, saturated $Na_2CO_3$ solution (210 mL) added and the mixture extracted with ethyl acetate (2×250 mL) and $CHCl_3$ (2×250 mL). The combined organic layers were dried and concentrated under reduced pressure. The residue was heated on a steam bath for 1.5 hours with 1.5N HCl (685 mL), the resulting solution cooled, and extracted with ether (2×300 mL). The acid layer was rendered alkaline with 20% NaOH solution and extracted with $CHCl_3$ (3×500 mL). The solvent was concentrated under reduced pressure and the residue was chromatographed on silica gel and eluted with 5% MeOH—$CHCl_3$ saturated with $NH_3$. The product was crystallized from acetonitrile to yield 4 (7.0 g, 25%, m.p. 122°-3° C.).

Anal. Calcd. for $C_{22}H_{26}N_2O_5$: C, 66.31; H, 6.58; N, 7.03. Found: C, 66.09; H, 6.69; N, 6.92.

EXAMPLE 2

(S)
2-{p-[3-(3,4-Dimethoxyphenylethyl)amino-2-hydroxypropoxy]phenyl}thiazole (9)

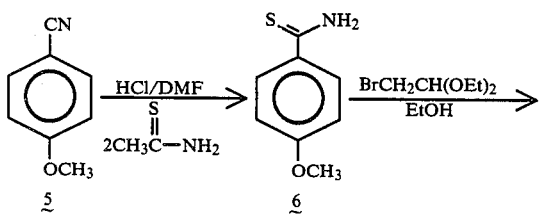

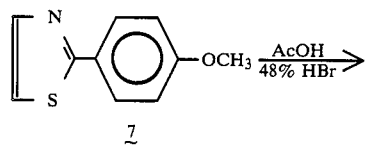

8

-continued

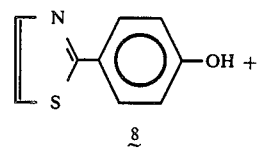

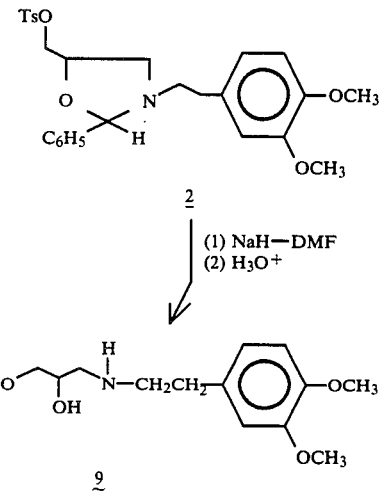

DMF (7 mL) was saturated with HCl and then thioacetamide (30 g, 0.4 mol) and p-anisonitrile (5) (21.6 g, 0.2 mol) were added. After heating the mixture on a steam bath for 0.5 hour, the DMF was concentrated under reduced pressure (0.5 mm). The residue was dissolved in hot saturated $NaHCO_3$ solution and the solution filtered. The aqueous solution was cooled and filtered to yield 6 Recrystallization from xylene yielded 21.7 g (65%) of 6; m.p. 143°-45° C. lit. 149° C.; $^1H$ NMR (DMSO-$d_6$) δ 3.5 (2H, each), 3.8 (3H, s), 6.9 (2H, d), 7.95 (2H, d).

A mixture of 6 (26.7 g, 0.16 mol), bromoacetaldehyde diethylacetal (31.5 g, 0.16 mol) and EtOH (75 mL) was heated at reflux. After 2 hours, the solution was concentrated to dryness and partitioned between saturated $NaHCO_3$ and $CHCl_3$ (3×). The organic extracts were dried, filtered and concentrated to dryness. The residue distilled at 110°-115° C. at 0.5 mm to yield 27.9 g (91%) of 7; $^1H$ NMR (CDCl$_3$) δ 3.85 (3H, s), 6.85 (2H, d, J=9), 7.15 (1H, d, J=3), 7.75 (1H, d, J=3), 7.85 (2H, d, J=9).

A solution of 7 (10.4 g, 0.054 mol), AcOH (50 mL) and 48% HBr (200 mL) was heated at reflux. After 2½ hours, the solution was concentrated to dryness, the residue treated with saturated $NaHCO_3$ to a pH 8.5 and stirred overnight at room temperature. The suspension was filtered to yield 8 which was recrystallized from EtOH to yield 7.8 g (81%) of 8; m.p. 163°-165° C. lit. m.p. 163°-165° C.

To a suspension of NaH (60% oil dispersion, 2.9 g, 0.073 mol) in DMF (100 mL) was added under $N_2$ with stirring a solution of 8 (13 g, 0.073 mol) in DMF (50 mL). After 15 minutes at 70° C. a solution of 2 (0.073 mol) in DMF (50 mL) was added dropwise and then heated to 120° C. with stirring. After 18 hours, the solution was poured into $H_2O$ and extracted with EtOAc (3×). The organic extracts were washed with $H_2O$, saturated NaCl, dried, filtered and concentrated to dryness. The residue was treated with $H_2O$ (500 mL) and AcOH (75 mL) and stirred at room temperature.

After 18 hours, the aqueous solution was extracted with EtOAc (2×), neutralized with saturated Na₂CO₃ and extracted with CHCl₃ (4×). The organic extracts were dried, filtered and concentrated to dryness. The residue was chromatographed on silica gel and the product eluted with 5% CH₃OH—CHCl₃ to yield 10 g of 9. Recrystallization from CH₃CN yielded 6 g (20%) of 9, m.p. 119°–120° C. ¹H NMR (DMSO-d₆) δ 2.75 (6H, m), 3.75 (3H, s), 3.8 (3H, s), 4.0 (3H, m), 7.85 (3H, m), 7.1 (2H, d, J=9), 7.5 (1H, d, J=3), 7.9 (1H, d, J=3), 7.95 (2H, d, J=9).

Analysis calc'd for $C_{22}H_{26}N_2O_4S$.

EXAMPLE 3

2-[p-(3-Cyclopropylamino-2-hydroxypropoxy)phenyl]-thiazole (11)

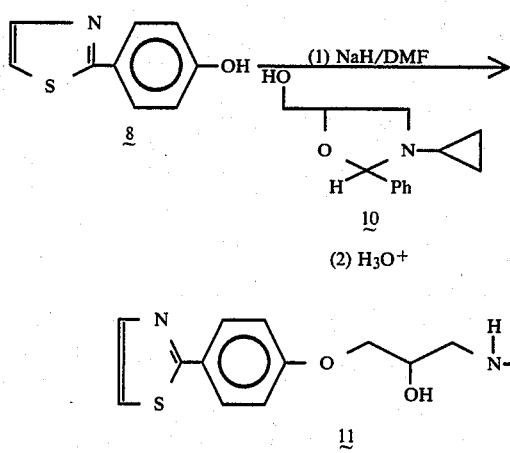

To a suspension of NaH (60% oil dispersion, 1.5 g, 0.037 mol) in DMF (50 mL), was added portionwise with stirring under N₂ 8 (6.5 g, 0.037 mol) and the mixture heated on a steam bath. After 15 minutes a solution of 10 (0.037 mol) in DMF (80 mL) was added dropwise. After heating overnight on a steam bath, the solution was poured into H₂O and extracted with EtOAc (3×) and the organic extracts washed with H₂O, saturated NaCl, dried, filtered and concentrated to dryness. The residue was treated with H₂O (0.50 mL) and AcOH (35 mL) and stirred overnight at room temperature. The aqueous layer was extracted with EtOAc, neutralized with saturated Na₂CO₃ and extracted with CHCl₃ (4×). The combined organic extracts were dried, filtered and concentrated to dryness. The residue was crystallized from CH₃CN to yield 3.5 g (33%) of 11; m.p. 100°–102° C.; ¹H NMR (CDCl₃) δ 0.35 (4H, m) 2.1 (1H, m), 2.75 (4H, m, 24CH), 3.95 (3H, m) 6.9 (2H, d, J=9), 7.2 (1H, d, J=3), 7.8 (1H, d, J-3), 7.85 (2H, d, J=9).

Analysis calc'd for $C_{15}H_{18}N_2O_2S$.

Using the procedures and methods described in the foregoing Reaction Scheme and Examples, additional compounds of Formula I can be prepared as set forth in Table I below.

TABLE I

Additional Compounds of Formula I

| | X | Positional Isomer | n | R |
|---|---|---|---|---|
| (a) | S | ortho | 0 | —CH(CH₃)₂ |
| (b) | " | meta | " | —CH₂CH₂—C₆H₅ |
| (c) | " | para | " | —C(CH₃)₃ |
| (d) | " | " | 1 | —(CH₂)₂CH₃ |
| (e) | " | meta | " | —CH₂CH₂—C₆H₄—OH |
| (f) | " | ortho | " | —CH₂CH₂—C₆H₄—Cl |
| (g) | " | para | " | CH₂CH₂—C₆H₃(OCH₃)₂ |
| (h) | " | meta | 2 | —C(CH₃)₃ |
| (i) | " | ortho | 1 | —CH(CH₃)₂ |
| (j) | O | " | 0 | CH₃CHCH₂CH₃ |
| (k) | " | meta | " | —CH(CH₃)₂ |
| (l) | S | para | " | —CH₂CH₂NHCNH—n-Bu (C=O) |
| (m) | " | " | " | —CH₂CH₂NHCNH—C₆H₅ (C=O) |
| (n) | " | para | " | —CH₂CH₂—C₆H₄—OH |
| (o) | " | ortho | " | —C(CH₃)₃ |
| (p) | " | para | " | —CH₂CH₂CH₂—C₆H₄—Br |
| (q) | " | meta | " | —C(CH₃)₂CH₂—C₆H₄—OCH₃ |
| (r) | " | para | 2 | —CH₂CH₂OCH₂CH₃ |
| (s) | " | ortho | 1 | " |
| (t) | O | para | 2 | —CH₂CH₂SCH₂CH₃ |
| (u) | " | " | 1 | —CH₂CH₂—C₆H₃(OCH₃)₂ |

In evaluating the β-blocking effectiveness of the present compounds, it was noted that the compounds exhibit cardioselectivity; that is, the compounds are more effective in reducing the heart rate effects of isoproterenol than they are in blocking the isoproterenol effects on the bronchi. Expressed in different terms, a smaller amount of a compound of the invention is required to block isoproterenol-induced elevation in heart rate than is required to block the isoproterenol-induced relaxation of the bronchi. This cardioselectivity factor can be expressed as the ratio of $ED_{50}$ for pulmonary effect $(\beta_2)$:$ED_{50}$ for cardiac effect $(\beta_1)$. Where the $\beta_2$:$\beta_1$ ratio is over 1, then the compound would be considered to have cardioselective activity.

Compounds of the invention which were tested and found to have $\beta_2$:$\beta_1$ ratios greater than 1 are shown in Table II below wherein the results obtained were determined according to the procedure described by Baldwin et al., *J. Med. Chem.*, 26, 956–7 (1983) pursuant to which in vitro $\beta$-adrenergic blocking activity is determined by the interaction with $\beta_1$-receptor via inhibition of the positive chronotropic actions of isoproterenol in isolated guinea pig atrial preparations. $\beta_2$ potency is determined by using isolated guinea pig tracheal chains contracted with $PGF_{2\alpha}$ and by measuring inhibition of isopreterenol-induced relaxation.

TABLE II

Compounds Having $\beta_2$:$\beta_1 > 1$

| Example | $\beta_1pA_2$ | $\beta_2pA_2$ | $\beta_2$:$\beta_1$ |
|---------|---------------|---------------|---------------------|
| 1 | 5.95 | 4.67 | 19 |
| 2 | 7.23 | 4.32 | 813 |
| 3 | 5.63 | 3.7 | 85 |

What is claimed is:

1. A compound which is a member of the group
2-{p-[3-(3,4-dimethoxyphenylethylamino)-2-hydroxypropoxy]phenyl}oxazole;
(S)-{p-[3-(3,4-dimethoxyphenylethyl)amino-2-hydroxypropoxy]phenyl}thiazole; and
2-[p-(3-cyclopropylamino-2-hydroxypropoxy)-phenyl]thiazole;
and, the pharmacologically acceptable acid addition salts thereof.

2. A pharmaceutical composition useful for treating hypertension and glaucoma or effecting $\beta$-adrenergic blockade comprising a pharmaceutically acceptable carrier; and, an antihypertensively, or ophthalmically, or $\beta$-adrenergic blockading effective amount of a compound of claim 1.

3. A method of treating hypertension and glaucoma or effecting $\beta$-adrenergic blockade comprising administering to a patient in need of such treatment an antihypertensively, or ophthalmically, or $\beta$-adrenergic blockading effective amount of a compound of claim 1.

* * * * *